United States Patent
Mukhopadhyay et al.

(10) Patent No.: US 6,812,223 B2
(45) Date of Patent: Nov. 2, 2004

(54) CRYSTALLINE GLUCOSAMINE SULFATE METAL SALTS AND PROCESSES FOR PREPARING THE SAME

(75) Inventors: Triptikumar Mukhopadhyay, Mumbai (IN); Ravi Gajanan Bhat, Mumbai (IN); E. S. Sreekumar, Maharashtra State (IN)

(73) Assignee: Nicholas Piramal India Limited (IN)

( * ) Notice: Subject to any disclaimer, the term of this patent is extended or adjusted under 35 U.S.C. 154(b) by 0 days.

(21) Appl. No.: 10/433,317
(22) PCT Filed: Dec. 3, 2001
(86) PCT No.: PCT/IN01/00211
§ 371 (c)(1),
(2), (4) Date: Jun. 2, 2003
(87) PCT Pub. No.: WO02/43653
PCT Pub. Date: Jun. 6, 2002

(65) Prior Publication Data
US 2004/0030121 A1 Feb. 12, 2004

(30) Foreign Application Priority Data
Dec. 1, 2000 (IN) .......................................... 1088/2000
Dec. 1, 2000 (IN) .......................................... 1087/2000
Apr. 26, 2001 (IN) ............................................ 394/2001

(51) Int. Cl.$^7$ ........................... A61K 31/70; C07H 5/06
(52) U.S. Cl. ........................ 514/62; 536/55.2; 536/121; 536/122; 536/55.3
(58) Field of Search .......................... 514/62; 536/55.2, 536/121, 122, 55.3

(56) References Cited

U.S. PATENT DOCUMENTS 4,642,340 A * 2/1987 Senin et al. ................ 536/55.2
5,843,923 A * 12/1998 Schleck et al. ............... 514/62
5,847,107 A * 12/1998 De Wan et al. ............ 536/55.3

* cited by examiner

Primary Examiner—James O. Wilson
Assistant Examiner—Michael C. Henry
(74) Attorney, Agent, or Firm—Pendorf & Cutliff

(57) ABSTRACT

The present invention relates to novel crystalline glucosamine sulphate metal salts for use in the treatment of acute and chronic forms of rheumatic and arthritic diseases and of all the pathological conditions originating from metabolic disorders of the osteo-articular tissues. More particularly, the present invention relates to novel crystalline glucosamine sulphate metal salts having low metal content wherein the metal may be either sodium or potassium. The present invention further relates to a solution-based and a solvent-free process for the preparation of the novel crystalline glucosamine sulphate metal salts having low metal content and to pharmaceutical compositions comprising the novel crystalline glucosamine sulphate metal salts having low metal content.

20 Claims, No Drawings

US 6,812,223 B2

CRYSTALLINE GLUCOSAMINE SULFATE METAL SALTS AND PROCESSES FOR PREPARING THE SAME

CROSS REFERENCE TO RELATED APPLICATION

This application is a national stage of PCT/IN01/00211 filed Dec. 3, 2001 and is based upon Indian Application Nos. 1087/MUM/2000, filed Dec. 1, 2000, 1088/MUM/2000, filed Dec. 1, 2000, and 394/MUM/2001, filed Apr. 26, 2001, under the International Convention.

FIELD OF THE INVENTION

The present invention relates to novel crystalline glucosamine sulphate metal salts for use in the treatment of acute and chronic forms of rheumatic and arthritic diseases and of all the pathological conditions originating from metabolic disorders of the osteo-articular tissues. More particularly, the present invention relates to novel crystalline glucosamine sulphate metal salts having low metal content wherein the metal may be either sodium or potassium. The present invention further relates to a solution-based and a solvent-free process for the preparation of the novel crystalline glucosamine sulphate metal salts having low metal content and to pharmaceutical compositions comprising the novel crystalline glucosamine sulphate metal salts having low metal content.

BACKGROUND OF THE INVENTION

Both acute and chronic forms of rheumatic and arthritic diseases are associated with joint pain and inflammation and hence cause a lot of distress to patients suffering from such a disease. Osteoarthritis, a degenerative joint disease, is the most common form of arthritis. This disease is mostly prevalent in older people. The standard therapy for the treatment of osteoarthritis mostly includes the use of aspirin, corticosteroids, non-steroidal anti-inflammatory drugs (NSAID's) e.g. ibuprofen, naproxen etc. and the most recent COX-2 inhibitors e.g. rofecoxib, celecoxib. However, all these drugs are associated with one or more side effects which may also be long term in some cases. An ideal treatment of osteoarthritis must effectively control pain as well as slow down or reverse the degeneration of joints and also cause fewer side effects. In the early 1970's it was discovered that a naturally occurring substance namely glucosamine can slow down the progression of osteoarthritis and also alleviate the pain associated with this disease [Kurtz J. F. et. al.: *Z. Allgemeinmed* 46(21): 1090–1095 (1970); Vinel P. et. al.: *Therapeutique*, 47(10): 839–843 (1971)].

Glucosamine (an amino saccharide) helps in strengthening the joint structure thereby improving mobility. So far four main sources of glucosamine are reported namely glucosamine hydrochloride, glucosamine hydroiodide, glucosamine sulphate and N-acetyl glucosamine. Of these, glucosamine sulphate is the most preferred form of glucosamine and is widely used in the treatment of osteoarthritis and other acute and chronic forms of rheumatic and arthritic diseases. The benefits of using glucosamine sulphate in the treatment of osteoarthritis and other arthritic diseases as well as the safety and efficacy of this drug are well proven [Dormant A. et. al.: *Clin. Ther.* 3(4): 260–272 (1980); Vaz. A. L.: *Curr. Med. Res. Opin.*; 8(3): 142–149 (1982); Tapadinhas M. J.: *Pharmaceutica* 3: 157–168 (1982); Reichelt A. et. al.: *Arzneim Forschung* 44: 75–80 (1994)].

Although highly effective, glucosamine sulphate is unstable in its free form due to its highly hygroscopic nature and also the amino group gets oxidised readily. Hence, oral formulations such as capsules, tablets of this drug contain anti-oxidants. However, this does not solve the problem of its hygroscopic nature. To overcome this problem glucosamine sulphate is usually combined with metal salts preferably sodium or potassium salts. Mixed salts of glucosamine hydrochloride with alkali metals or alkaline earth metal sulphates such as sodium or potassium sulphates are well known in the literature. Usually glucosamine sulphate metal salts are prepared starting from either glucosamine hydrochloride or the glucosamine free base.

Preparation of glucosamine sulphate is described in GB Patent No. 1056331, U.S. Pat. No. 3,683,076 and Swiss Patent No. 525861.

Preparation of mixed salt of glucosamine sulphate and sodium chloride is described in U.S. Pat. No. 4,642,340 wherein previously prepared glucosamine sulphate is treated with sodium chloride solution followed by addition of liquid precipitant to precipitate the mixed salt. This process involves direct use of glucosamine sulphate which has to be strictly maintained in an environment with a relative humidity not greater than 30% and a temperature not more than 15° C., thus one has to take proper precautions in this case.

EP 214642 describes a process for the preparation of mixed salt of glucose sulphate and potassium chloride starting from glucosamine free base wherein solution of the glucosamine free base in water is treated with concentrated sulphuric acid and to the resulting solution potassium chloride is added. The metal salt is precipitated out from the solution by adding liquid precipitant. This is a lengthy process since it first involves liberation of free glucosamine base from glucosamine hydrochloride followed by the subsequent reaction steps. Also this process results in low yield.

U.S. Pat. No. 5,847,107 teaches a process for preparing crystalline form of mixed glucosamine sulphate salts wherein glucosamine hydrochloride is treated with a metal sulphate e.g. sodium sulphate in an aqueous solvent and the stable crystalline form of glucosamine sulphate is precipitated from the solution by adding a liquid precipitant.

U.S. Pat. Nos. 5,843,923 and 5,902,801 follow the same method for the preparation of glucosamine sulphate metal salts, however, in these cases the process avoids addition of liquid precipitating agent but involves freeze drying of the solution resulted from the reaction of glucosamine hydrochloride and metal sulphate.

Although, the mixed glucosamine sulphate metal salts, the products described in U.S. Pat. Nos. 5,847,107 and 5,902,801, are suitable for treatment of rheumatic and arthritic diseases, they have proportionately high metal content e.g. sodium or potassium. Rheumatic and arthritic diseases are mostly prevalent in older people who are also at higher risk of other diseases such as hypertension and cardiovascular diseases. Hyperkalemia (high potassium level) is also a serious electrolyte disorder which appears to develop more commonly in the aged patients. In such cases the patients are advised a restricted sodium or potassium intake depending on the case history. Also people suffering from renal dysfunction require low sodium intake. Therefore, administration of glucosamine sulphate mixed salts having proportionately high sodium or potassium content may not be advisable to those rheumatic or arthritic patients who are also having history of hypertension, cardiovascular diseases, renal dysfunction, hyperkalemia and other diseases which require restricted sodium or potassium intake. Taking into account the proven safety and efficacy of glucosamine sulphate over other conventional drugs for arthritic diseases, there is a need to develop a specific form of glucosamine sulphate which can also be safely administered to sodium or potassium sensitive patients.

The present inventors have now found novel crystalline glucosamine sulphate metal salts having low metal content, wherein the metal may be either sodium or potassium. The use of the crystalline glucosamine sulphate sodium or potassium salt of the present invention, is not only an efficacious treatment for all arthritic patients but also a safer remedy for those patients who are also having history of diseases which require restricted sodium or potassium intake.

OBJECTS OF THE INVENTION

The primary object of the invention aims at providing novel crystalline glucosamine sulphate metal salts having low metal content, useful in the treatment of acute and chronic forms of rheumatic and arthritic diseases and of all the pathological conditions originating from metabolic disorders of the osteo-articular tissues.

Another object of the present invention is to provide novel crystalline glucosamine sulphate metal salts having low metal content, wherein the metal may be either sodium or potassium, as efficacious and safer remedy to sodium or potassium sensitive arthritic patients.

Yet another object of the invention is to provide a solution-based process and a solvent-free process for the preparation of the crystalline glucosamine sulphate metal salts having low metal content.

A further object of the invention is to provide a pharmaceutical composition containing the novel crystalline glucosamine sulphate metal salts having low metal content.

SUMMARY OF THE INVENTION

Thus in accordance with the present invention there is provided novel crystalline glucosamine sulphate metal salts having low metal content, which are represented by the following formula I:

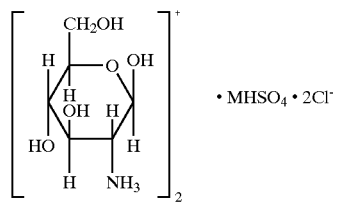

wherein M represents Na or K (hereinafter referred to as compound I).

In compound I (M=Na), the amount of sodium content is only 4.22% as against 8% of sodium that is present in the mixed glucosamine sulphate sodium salt, the product described in the prior art (U.S. Pat. Nos. 5,847,107 and 5,902,801). Also the potassium content in compound I (M+K) is only 7.16% as against 12.9% of potassium that is present in the product described in U.S. Pat. Nos. 5,847,107 and 5,902,801.

Thus, the compounds of formula I of the present invention are significantly advantageous over those reported in the prior art with respect to their usefulness specifically in the treatment of arthritic patients who are sodium and potassium sensitive.

According to a further aspect of the present invention there is provided a solution-based process for the preparation of compounds of formula I, which comprises the steps of:

i. reacting glucosamine hydrochloride and a metal hydrogen sulphate selected from sodium hydrogen sulphate and potassium hydrogen sulphate in stoichiometric ratio in a solvent;
ii. precipitating the resulting glucosamine sulphate metal salt in the presence of a water miscible organic solvent;
iii. filtering the reaction mass to obtain the compound of formula I.

In the above process the solvent used in the reaction step (i) can be water. Also, the said steps of precipitating the resulting glucosamine sulphate metal salt can comprise either adding the resulting solution of step (i) to a water-miscible organic solvent or the water-miscible organic solvent to the resulting solution of step (i), followed by stirring the resulting solution obtained for a predetermined period of time. This well stirred reaction mass is then filtered to obtain the desired compound of formula I.

According to another aspect of this invention, prior to the step of filtering the reaction mass in step (iii) the reaction mass is allowed to cool for a predetermined period of time and then filtered to obtain the desired compound of formula I.

The term stoichiometric ratio in the solution-based process refers to 2:1 ratio of glucosamine hydrochloride to the metal hydrogen sulphate.

The water-miscible organic solvent may be selected from ethanol, propanol, isopropanol, acetone, acetonitrile, tetydrofuran, dioxane, dimethylformamide and the like. The most preferred solvent is isopropanol.

The water-miscible organic solvent is taken in a proportion of four to ten parts by volume with respect to solution of step (i). Preferably solution of step (i) is added to six times its volume of the water-miscible solvent.

The time period required for the addition might vary from five minutes to four hours, preferably one hour.

The addition of the resulting solution of step (i) to the water-miscible organic solvent or the addition of the water-miscible organic solvent to the resulting solution of step (i) is carried out room temperature ranging from 17° C. to 35° C. preferably 20 to 25° C.

The resultant mixture containing the precipitate is stirred for a period of about 2 to 6 hours preferably 4 hours at room temperature ranging from 17° C. to 35° C. preferably 20 to 25° C. This well stirred reaction mass is then filtered under vacuum. The product is washed to obtain glucosamine sulphate salt as white solid and is further dried at 25° C. under vacuum.

According to another aspect of this invention, this well stirred mass may be cooled to 0–20° C., preferably 0–10° C., more preferably 0–5° C., and maintained at this temperature for about 1–24 hours preferably 1–20 hours more preferably 1–16 hours. The reaction mass is then filtered under vacuum. The product is washed to obtain glucosamine sulphate salt as white solid and is further dried at 25° C. under vacuum.

According to another aspect of the invention, there is provided a solvent-free process for the preparation of compounds of formula I, which comprises pulverizing a mixture of glucosamine hydrochloride and a metal hydrogen sulphate in a stoichiometric ratio at ambient temperature over a predetermined period of time.

The term stoichiometric ratio in the solvent-free process refers to 2:1 ratio of glucosamine hydrochloride to a metal hydrogen sulphate.

The term ambient temperature in the solvent-free process refers to room temperature ranging from 17° C. to 35° C., preferably 20 to 25° C.

The pulverization of the mixture is carried out by using an appropriate device such as a ball mill, a multi mill, a hammer mill and the like; or a mortar and pestle. Preferably mortar and pestle is used for the pulverization.

The pulverization is carried out over a period ranging from 0.2 hours to 2 hours, preferably 0.5 hours to 1 hour.

Compounds I according to present invention are stable at ambient temperature and humidity. The yield of the product is between 75% to 85%, when the solution—based process is employed. The yield of the product is between 97% to 99.5%, when the solvent-free process is employed.

The compounds of formula I of the present invention are suitable for use in the treatment of both acute and chronic forms of rheumatic and arthritic diseases, in particular osteoarthritis and generally, of all pathological conditions originating from metabolic disorders of the osteo-articular tissues.

The compounds of the present invention may be administered preferably in the form of oral formulations such as tablets or capsules or in injectable form. Other forms of formulations containing the compounds of the present invention are also included within the scope of this invention.

Thus, in a further aspect of the present invention there is provided a pharmaceutical composition comprising compound I of the present invention. The pharmaceutical composition according to the present invention may be prepared by standard techniques by mixing the compound I with one or more pharmacologically acceptable excipients and/or auxiliaries such as fillers, emulsifiers, lubricants, masking flavour colorants or buffer substances, and converting the mixture into a suitable pharmaceutical form such as tablets, coated tablets, capsules or a suspension or solution suitable for parenteral administration.

The scope and objects of the present invention may further be illustrated by the following examples, which may not be considered to be limiting the invention in any manner.

EXAMPLE 1

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was added dropwise to vigorously stirred isopropanol(150 ml) at room temperature over a period of one hour. The contents in the flask were further stirred for 4 hrs and then kept at 0° C.–5° C. for 16 hrs. The precipitate was filtered under vacuum (150 mm Hg). The product was washed twice (each time with 25 ml of isopropanol).

Glucosamine sulphate salt was obtained as white solid and was further dried at 25° C. under vacuum (2 mm Hg).

| | |
|---|---|
| Yield | 6.6 g |
| Melting Point | >300° C. |
| $[\alpha]_D^{25}$ | +59° (c2, water) |
| Sodium content | 4.22% |

EXAMPLE 2

Preparation of Glucosamine Sulphate Potassium Salt (Low Potassium Content)

Glucosamine hydrochloride (6.45 g, 0.03 mol) and potassium hydrogen sulphate (2.040 g, 0.015 mol).were taken in a flask and dissolved in water (25 ml). The resulting solution was added dropwise to vigorously stirred isopropanol (150 ml) at room temperature over a period of one hour. The contents in the flask were further stirred for 4 hrs and then kept at 0° C.–5° C. for 16 hrs. The precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| | |
|---|---|
| Yield | 6.94 g |
| Melting Point | >300° C. |
| $[\alpha]_D^{25}$ | +58.5° (c2, water) |
| Potassium content | 7.16% |

EXAMPLE 3

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was vigorously stirred and to this isopropanol (150 ml) was added dropwise at 25° C. (room temperature) over a period of one hour. The contents in the flask were further stirred for 4 hrs and then kept at 0° C.–5° C. for 16 hrs. The precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| | |
|---|---|
| Yield | 6.34 g |
| Melting Point | >300° C. |
| $[\alpha]_D^{25}$ | +60° (c2, water) |

EXAMPLE 4

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was added dropwise to vigorously stirred isopropanol (150 ml) at room temperature over a period of one hour. The contents in the flask were further stirred for 4 hrs and the precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| | |
|---|---|
| Yield | 6.35 g |
| Melting Point | >300° C. |
| $[\alpha]_D^{25}$ | +60.6° (c2, water) |

EXAMPLE 5

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was added dropwise to vigorously stirred isopropanol(150 ml) at room temperature over a period of one hour. The contents in the flask were further stirred for 4 hrs and then kept at 0° C.–5° C. for 2 hrs. The precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| Yield | 6.86 g |
|---|---|
| Melting Point | >300° C. |
| $[\alpha]_D^{25}$ | +60.4° (c2, water) |

EXAMPLE 6

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was added dropwise to vigorously stirred isopropanol (150 ml) at room temperature over a period of one hour. The contents in the flask were further stirred for 4 hrs and then kept at 0° C.–5° C. for 4 hrs. The precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| Yield | 6.9 g |
|---|---|
| Melting Point | >300° C. |
| $[\alpha]_D^{25}$ | +59.5° (c2, water) |

EXAMPLE 7

Preparation of Glucosamine Sulphate Sodium Salt (Low Sodium Content)

Glucosamine hydrochloride (6.45 g, 0.03 mol) and sodium hydrogen sulphate (1.8 g, 0.015 mol) were taken in a flask and dissolved in water (25 ml). The resulting solution was added to vigorously stirred isopropanol(150 ml) at room temperature over a period of five minutes. The contents in the flask were further stirred for 4 hrs and then kept at 0C.–5° C. for 16 hrs. The precipitate was filtered under vacuum (150 mm Hg). The product was washed twice (each time with 25 ml of isopropanol). Glucosamine sulphate salt was obtained as white solid and was further dried at 25° C. under vacuum (2 mm Hg).

| Yield | 6.68 g |
|---|---|
| Melting Point | >300° C. |
| $[\alpha]_D^{25}$ | +60.0° (c2, water) |

EXAMPLE 8

Glucosamine hydrochloride (12.9 g, 0.06 mol) was added to sodium hydrogen sulphate (3.6 g, 0.03 mol) and the mixture was pulverised by using a mortar and pestle to obtain the Glucosamine sulphate salt.

| Yield | 16.1 g |
|---|---|
| Melting Point | >300° C. |
| $[\alpha]_D^{25}$ | +51° (c2, water) |

Estimation of Metal Content in the Mixed Glucosamine Sulphate Metal Salt

The sodium content in the mixed glucosamine sulphate sodium salt or the potassium content in the mixed glucosamine sulphate potassium salt respectively is estimated using Inductively Coupled Plasma Method. The sodium content was measured at 589.592 nm and the potassium content was measured at 766.491 nm.

| Instrument | Inductively Coupled Plasma Spectrometer |
|---|---|
| Model | Spectroflame Modula Type FSM A 81A |

We claim:
1. Glucosamine sulphate metal salts having low metal content, which are represented by the following formula I:

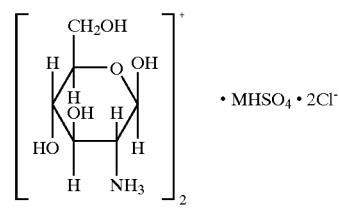

wherein M represents a metal selected from the group consisting of Na (sodium) and K (potassium).
2. The salt of claim 1 wherein M is Na (sodium).
3. The salt of claim wherein M is K (potassium).
4. A method for the preparation of the compound according to formula I,

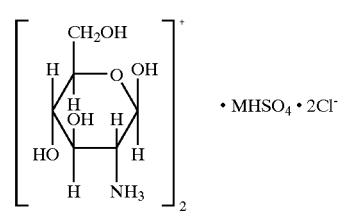

wherein M is K (potassium) or Na (sodium), said method comprising the steps of:
  (i) reacting glucosamine hydrochloride and a metal hydrogen sulphate of formula

MHSO$_4$ in a stoichiometric ratio in an aqueous solvent to obtain said glucosamine sulphate metal salt;
  (ii) precipitating the resulting glucosamine sulphate metal salt contained in the resulting solution of step (i) using a water miscible organic solvent; and
  (iii) filtering the reaction mass obtained in step (ii) to yield said glucosamine sulphate metal salt of formula I.

5. The method of claim 4 wherein said aqueous solvent of step (i) is water.

6. The method of claim 4 wherein said step (ii) of precipitating the resulting glucosamine sulphate metal salt comprises either adding the resulting solution of step (i) to the water-miscible organic solvent, or adding the water-miscible organic solvent to the resulting solution of step (i), at an appropriate temperature for a predetermined period of time, followed by stirring the resulting reaction mixture.

7. The method of claim 6 wherein said addition is carried out at a temperature ranging from 17° C. to 35° C.

8. The method of claim 6 wherein said addition is carried out over a period of five minutes to four hours.

9. The method of claim 4 wherein the ratio of the resulting solution of step (i) to the water-miscible organic solvent of step (ii) ranges from 1:4 to 1:10.

10. The method of claim 4 wherein said water-miscible organic solvent is selected from the group consisting of ethanol, propanol, isopropanol, acetone, acetonitrile, tetrahydrofuran, dioxane, dimethylformamide, and the like, or a mixture thereof.

11. The method of claim 6 wherein stirring of the resulting reaction mixture is carried out at an appropriate temperature for a predetermined period of time.

12. The method of claim 11 wherein stirring of the resulting reaction mixture is carried out for a period of 2 to 6 hours.

13. The method of claim 11 wherein stirring of the reaction mixture is carried out at a temperature ranging from 17° C. to 35° C.

14. The method of claim 4 wherein said step (iii) of filtering the reaction mass is preceded by cooling of the reaction mass to an appropriate temperature and maintaining it at said temperature for a predetermined period of time.

15. The method of claim 14 wherein said reaction mass is cooled to 0–20° C.

16. The method of claim 14 wherein said reaction mass is maintained at said temperature for a period of 1–24 hours.

17. A method for the preparation of the compound of formula I:

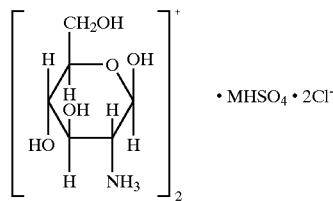

wherein M is K (potassium) or Na (sodium), said method comprising the step of pulverizing, using an appropriate device, a mixture of glucosamine hydrochloride and a metal hydrogen sulphate of formula,

MHSO$_4$ in a stoichiometric ratio at an ambient temperature over a predetermined period of time.

18. The method of claim 17 wherein said pulverization is carried out over a period ranging from 0.2 hours to 2.0 hours.

19. A pharmaceutical composition comprising as effective amount of a crystalline glucosamine sulphate metal salt according to formula I:

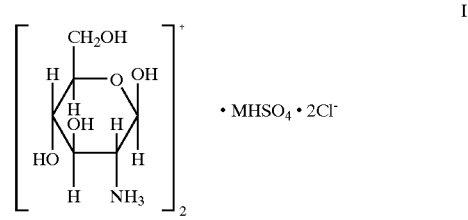

wherein said salt has a low metal content and wherein M represents a metal selected from the group consisting of Na (sodium) and K (potassium).

20. A method for the treatment of a disease, said method comprising administering to a subject in need thereof an effective amount of a pharmaceutical composition comprising a crystalline glucosamine sulphate metal salt according to formula I:

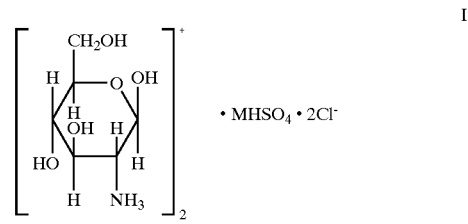

wherein said salt has a low metal content and wherein M represents a metal selected from the group consisting of Na (sodium) and K (potassium), and wherein said disease is selected from the group consisting of acute rheumatism, chronic rheumatism, acute arthritis, chronic arthritis, and a pathological condition arising from a metabolic disorder of an osteo-articular tissue.

* * * * *